(12) United States Patent
Jain et al.

(10) Patent No.: US 8,334,767 B2
(45) Date of Patent: Dec. 18, 2012

(54) METHOD AND SYSTEM FOR FACILITATING AUTOMATED NAVIGATION IN A HEALTHCARE ENVIRONMENT

(75) Inventors: Rachit Jain, Karnataka (IN); Ramkumar Saptharishi, Karnataka (IN); Monika Jain, Karnataka (IN)

(73) Assignee: General Electric Company, Schenectady, NY (US)

( * ) Notice: Subject to any disclaimer, the term of this patent is extended or adjusted under 35 U.S.C. 154(b) by 434 days.

(21) Appl. No.: 12/634,716

(22) Filed: Dec. 10, 2009

(65) Prior Publication Data

US 2010/0176941 A1    Jul. 15, 2010

(30) Foreign Application Priority Data

Jan. 12, 2009  (IN) .............................. 90/CHE/2009

(51) Int. Cl.
*G08B 1/08* (2006.01)

(52) U.S. Cl. ........... 340/539.13; 340/539.26; 340/572.1; 340/572.4; 340/572.7; 340/573.1; 70/439; 70/466; 70/469

(58) Field of Classification Search ............. 340/539.13, 340/539.26, 572.1–572.7, 573.4; 701/206–213, 701/439, 466, 469
See application file for complete search history.

(56) References Cited

U.S. PATENT DOCUMENTS

| | | | | |
|---|---|---|---|---|
| 5,842,145 A | * | 11/1998 | Zimmer ........................ | 701/533 |
| 6,622,088 B2 | * | 9/2003 | Hood ............................ | 701/517 |
| 6,924,741 B2 | * | 8/2005 | Tamayama et al. ......... | 340/572.1 |
| 7,880,610 B2 | * | 2/2011 | Tanner et al. ............. | 340/539.26 |
| 2007/0146136 A1 | | 6/2007 | Chen et al. | |

FOREIGN PATENT DOCUMENTS

WO    2007072389 A1    6/2007

* cited by examiner

*Primary Examiner* — Tai T Nguyen
(74) *Attorney, Agent, or Firm* — Global Patent Operation

(57) ABSTRACT

A method and system for facilitating automated navigation in a healthcare facility. The navigation system comprises: a healthcare information system configured to have access to at least patient information, healthcare resource information and healthcare facility information; and an identification device provided to a patient in the healthcare facility, configured to communicate at least the current location of the patient to the hospital information system. The identification device and the healthcare information system interact with each other for generating and providing at least navigation information to the patient.

20 Claims, 9 Drawing Sheets

METHOD AND SYSTEM FOR FACILITATING AUTOMATED NAVIGATION IN A HEALTHCARE ENVIRONMENT

CROSS-REFERENCE TO RELATED APPLICATIONS

This application claims priority under 35 U.S.C. §119(a)-(d) or (f) to prior-filed, co-pending Indian patent application serial number 90/CHE/2009, filed on Jan. 12, 2009, which is hereby incorporated by reference in its entirety.

BACKGROUND OF THE INVENTION

1. Field of the Invention

This invention relates generally to management of various healthcare resources and healthcare facilities in a healthcare environment, and more particularly to, a method and system for facilitating automated navigation in a healthcare environment. The invention is particularly useful in assisting patients in navigating in a healthcare facility.

2. Description of Related Art

Currently, a healthcare environment includes various healthcare resources, departments, healthcare facilities, clinicians etc located at different locations in the healthcare environment. For example, diagnostic labs, diagnostic equipments, emergency patient care room, admission and discharge section, billing facility, clinicians etc may be scattered at different parts of a hospital. Many times, in a healthcare environment such as hospital, the patient or the caretaker has to move from one locality to another, multiple times.

Mostly, the patient or the caretaker will consult a hospital staff to navigate to a desired destination. In a healthcare facility, there may be signboards indicating direction to various departments. But these signs boards give the patients or the caretaker an obtuse or vague navigation information and the patient may miss his way, as the intuitive details are not available.

Some of the hospitals have maps displayed indicating locations of various healthcare facility and resources. However if the patient is new to the hospital or if not able to understand the map or instructions provided along with it, the display of maps will not be helpful.

Further, the signboards and maps displayed are difficult to update and many times the maps or displays convey wrong navigation information to the patient, as they may not have been updated periodically.

Some of the solutions suggest, providing tracking devices with the patient as well as at the destination location. This will help, if the patient is in trauma and needs to locate a destination urgently. The tracking devices communicate with each other and the patient is navigated to the destination automatically. However, this requires providing tracking devices with the patient as well as at the destination and a server for managing the communication between them. Since the tracking devices are expensive and the information from both the tracking devices are required to navigate the patient efficiently, the process become more complicated and expensive. Thus it will be beneficial to have a simple and cost effective method for navigating in a healthcare environment.

Thus there exists a need to provide an improved method and system for navigating in a healthcare environment.

BRIEF SUMMARY OF THE INVENTION

The above-mentioned shortcomings, disadvantages and problems are addressed herein which will be understood by reading and understanding the following specification.

One embodiment of the present invention provides a system for assisting a patient in navigating within a healthcare environment. The system comprises: a healthcare information system configured to have access to at least patient information, healthcare resource information and healthcare facility information; and an identification device provided to a patient in the healthcare environment, configured to communicate at least the current location of the patient to the hospital information system. The identification device and the healthcare information system interact with each other for generating and providing at least navigation information to the patient.

In another embodiment, an automated navigation method in a healthcare environment is disclosed. The method comprises: providing an identification device to each patient in the healthcare facility, the identification device configured to identify current location of the patient; generating navigation information for the patient with reference to the current location of the patient; and communicating the navigation information to the identification device.

In yet another embodiment, a machine readable medium or media having recorded thereon instructions configured to instruct an apparatus comprising a server and an identification device for automatically navigating in a healthcare environment is disclosed. The medium comprises: a routine for obtaining the current location of a patient in a healthcare facility from an identification device provided to the patient; a routine for generating navigation information to a destination, for the patient with reference to the current location of the patient; and a routine for communicating the navigation information to the identification device.

Various other features, objects, and advantages of the invention will be made apparent to those skilled in the art from the accompanying drawings and detailed description thereof.

DETAILED DESCRIPTION OF THE INVENTION

Figure 1:
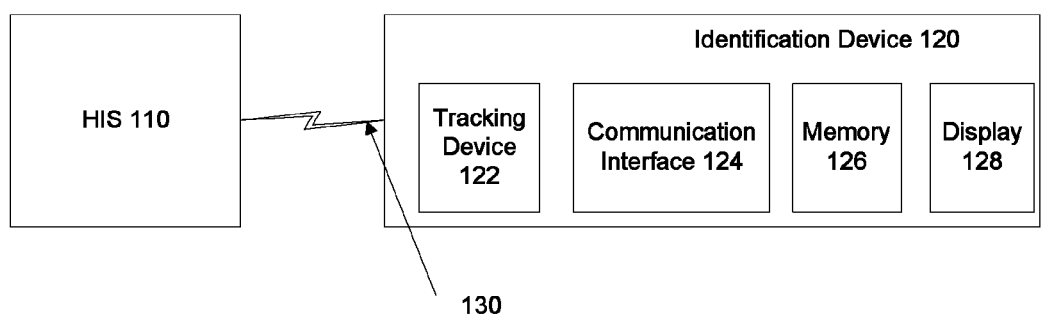
FIG. 1 is a block diagram of an automated navigation system as described in an embodiment of the invention.

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

Embodiments of the present invention assist a patient in navigating in a healthcare environment. To achieve this, an exemplary embodiment of the present invention utilizes a method of providing an identification device to the patient. The identification device communicates with a server or a healthcare information system (HIS) and obtains the navigation information corresponding to its destination. The identification device is provided only with the patients and is configured to convey the current location of the patient.

In an embodiment, an interactive healthcare facility map is generated with the details of healthcare facility and healthcare resources. This map is sent to the identification device and the same is stored in the identification device so that in the event of loosing communication with the hospital information system, the map can be retrieved by the identification device.

FIG. 1 is a block diagram of an automated navigation system as described in an embodiment of the invention. The system comprises a healthcare information system (HIS) 110 and an identification device 120. The HIS 110 is configured to receive patient information, healthcare facility information, healthcare resource information etc. Using the healthcare facility information and healthcare resource information, the HIS 110 may generate an interactive healthcare facility map. This map includes spatial direction and location to various healthcare facility and resources and also can have distance co-ordinate map of different locations. The HIS 110 may generate and store the map in a database. Alternately, an administrator may collect all the location information of healthcare resources, healthcare facility and generate a healthcare facility map and store it in HIS 110.

Figure 2:
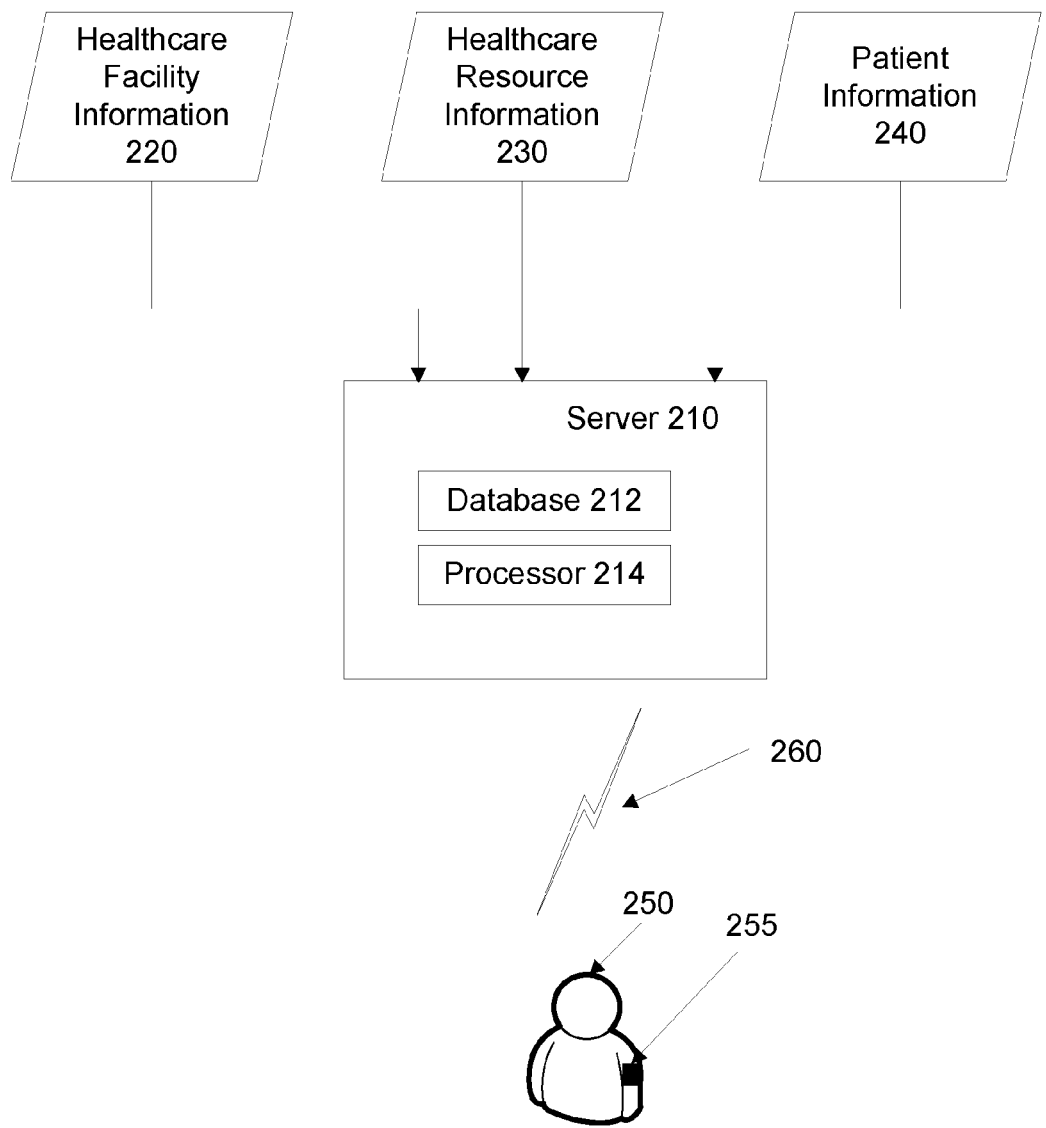
FIG. 2 illustrates a diagrammatic representation of an automated navigation system as described in an embodiment of the invention.

In an exemplary embodiment HIS maybe a server associated with a database and a processor as shown in FIG. 2.

In an embodiment, an identification device 120 is provided with each patient in the healthcare facility. The identification device 120 is configured to communicate with the HIS 110 in assisting patient in navigating within the healthcare facility. The identification device 120 communicates with the HIS 110 for obtaining navigation information corresponding to a destination.

In an embodiment, the identification device 120 includes a tracking device 122 operating based on tracking techniques such Radio frequency identification tag (RFID) based tracking device, Global positioning system (GPS) based tracking device, Infrared (IR) based tracking device, barcode based tracking device etc. The identification device 120 further comprises a communication interface 124, a memory 126 and a display 128. The tracking device 122 is configured to identify the current location of the patient and communicate the same to HIS 110 through the communication interface 124.

Also, the identification device 120 may be provided with destination information. The destination information indicates, a desired destination facility or the resource to which the patient needs to navigate. An administrator may provide this information to the identification device 120. Alternately, the administrator may communicate patient information along with the destination to the HIS 110.

Each patient in the healthcare facility may be provided with an identification device 120. Before assigning it to each patient, the identification device 120 is configured using the patient identification information for that patient. In an example, a unique ID identifies each identification device 120 and the unique ID can be formatted using patient information. This unique ID may be provided with HIS 110 to identify the patient.

In the hospital or healthcare environment, a communication network is established for facilitating communication among various resources present in the healthcare facility. The HIS 110 may directly interact with the identification device 110 or may communicate through a server (not shown). If both identification device 120 and the HIS 110 are in the same communication network, they may establish communication through a wireless communication link 130 either directly or through a server. Once the communication is established, the identification device 120 communicates the current location of the patient along with the destination. Alternately, the destination may be sent to HIS 110 by an administrator separately, while giving the destination information to the patient.

In an embodiment, the destination information may be given to the identification device 120 by an administrator or by patient. The destination information along with the patient information may be conveyed to the HIS 110. The HIS 110 may verify the unique ID of the identification device 120 before establishing communication among them. Upon establishing the communication, the HIS 110 may send the facility map to the identification device 120, and the identification device 120 may store the same in its memory 126. The identification device 120 tracks the current location of the patient and sends it to the HIS 110. The HIS 110 with the help of the facility map and the current patient location and destination, navigation information corresponding to the destination is derived. In an embodiment, the navigation information may include the direction and distance to the desired location from the current patient location.

In an embodiment, upon getting the knowledge about the destination, the HIS 110 may forward information relevant to the destination to the patient. For example, if a patient is going to a dental clinic, relevant information such as nearest follow up center near to patient's residence, nearest pharmacy shop etc may be communicated to the patient. Also HIS 110 may communicate some general information such as location of nearest emergency room, restrooms etc on the way to the destination. Additionally, HIS 110 may communicate, some promotional articles related to the destination to the patient. For example, if a patient is moving to an ENT department, dental care promotions may be send to the patient.

In an embodiment, the navigation information is conveyed to the patient through the display 128. The display 128 may be visual and/or audio display. The navigation information may be displayed in a visual display such as a monitor, LED, display, CRT screen etc, but examples of display need not be limited to this. Alternately, the navigation information may be conveyed to patient in an audio display. The display 128 may be a speaker and the navigation information may be announced through the speaker to the patient. This will help to assist the patients who are not able to read and understand the navigation information from the display 128.

Once the destination is arrived, the identification device 120 may beep or vibrate.

Further, the identification device 120 and the HIS 110 may exchange the current location and navigation information continuously or at a preset interval. Optionally, as and when the patient get stuck somewhere, the patient may communicate with HIS 110 to obtain the navigation information. Also, the patient may query HIS for some relevant information from HIS.

Further more, to provide additional security, the identification device 120 may be provided with a password. The password may be formatted using patient specific information such as his blood group, biometric information, date of birth etc. However the password may be set at the patient's convenience. In case of establishing an initial communication or re establishing a communication with the HIS 110, the HIS 110 may ask for the password and verify the same before establishing the communication. Also the HIS 110 may verify the password periodically, to prevent misuse of the identification device 120.

In an embodiment, the patient may be faced with an emergency situation on the way to the destination. The patient may communicate this to the HIS 110. In an example the identification device 120 may be provided with an emergency button (not shown) and in case of an emergency, the patient can communicate with the HIS 110 by pressing the emergency button. Once the emergency button is pressed, the identification device 120 communicates the current patient location with an emergency signal to the HIS 110. The HIS 110 will identify the nearest emergency patient care room and communicate the patient location and patient information to the identified emergency room. The nearest emergency room location may be conveyed to the patient. The emergency room may establish a communication with the patient and a clinician may talk to the patient.

Additionally, the identification device 120 may be provided with a configurable button, configured to achieve different functionality. Alternately, the emergency button may be configured to perform different functions. The buttons may be programmable or can have different keys or touch panel to type in different queries and send it to the HIS 110.

In an exemplary embodiment, the identification device 120 may be associated with a patient moving device (not shown) such as wheelchair, patient table etc and the location information may be given to the patient moving device directly and the patient may be moved automatically to the desired destination.

In an embodiment, the HIS 110 may be provided with traffic information towards a healthcare facility. For example, in the event of patient heading towards an ENT department, the HIS 110 may communicate to the patient about the waiting information. This is achieved by providing the patient flow in the ENT department in real time to the HIS 110.

In an embodiment, an administrator may communicate with the patient through the HIS. In case administrator wanted to communicate to the patient urgently who is on his way to destination, the administrator may interact with the HIS and communicate the information that need to be conveyed to the patient to the HIS. The HIS may communicate this to the patient.

In an embodiment, any changes in the facility information or the resource information, it may be communicated to the HIS. If the information is relating to change in the location of the resource or facility, the same is updated in the interactive healthcare facility map. The updated map is communicated to the identification device 120. The update may be done in real time. The information might also include other relevant information relating to the resource and the facility. For example, if a resource is not operational or busy, the HIS may convey that to the patient and may suggest any other alternatives, if possible.

In an embodiment HIS 110 is any server in a healthcare environment, to which the identification device 120 can communicate wirelessly. The server might be associated with a database and a processor. The details are explained with reference to FIG. 2.

FIG. 2 illustrates a diagrammatic representation of a navigation system as described in an embodiment of the invention. The system includes: a server 210 configured to include a database 212 and processor 214. The server 210 may be a hospital server configured to interact with various devices in a healthcare network. The server 210 may be provided with healthcare resource information 230, healthcare facility information 220, and patient information 240. An administrator may provide this information to the server 210 and it may be stored in the database 212. The database 212 may also be provided with the patient information along with a unique identification number corresponding to the patient. The database 212 is stored in a memory. In an embodiment, the map may be stored in a portable memory and may be fed to the database in the server.

For purposes of simplicity, devices that can read and/or write media on which computer programs are recorded are also included within the scope of the term "memory." A non-exhaustive list of media that can be read with such a suitable device includes CDs, CD-RWs, DVDs of all types, magnetic media (including floppy disks, tape, and hard drives), flash memory in the form of sticks, cards, and other forms, ROMs, etc., and combinations thereof. The memory may also include random access memory (RAM), read-only memory (ROM), electrically programmable memory (EPROM) etc.

The processor 214 configured to generate an interactive healthcare facility map using the healthcare resource information 230, healthcare facility information 220. The map will indicate detailed layout of a hospital with location of different departments, location of various medical device, orientation, distance co ordinates etc. The processor 214 may also be configured to have the encryption and decryption information of the identification device 255. The processor may include dedicated hardware or software and/or firmware or a combination of dedicated hardware and software, or software in combination with a general purpose processor, or a digital signal processor. Once the requirements for such software and/or hardware and/or dedicated hardware are gained from an understanding of the descriptions of embodiments of the invention contained herein, the choice of any particular implementation may be left to a hardware engineer and/or software engineer.

In an embodiment, a patient 250 in the healthcare facility is provided with an identification device 255. The identification device 255 is configured for a patient 250 using the patient information 240 and this information is being sent to the server 210 as well.

In an embodiment the identification device 255 includes an RFID based tracking device, a GPS based tracking device, an IR based tracking device or a barcode based tracking device. The identification device 255 further includes a display and the memory.

The identification device 255 associated with the patient 250 is configured to communicate with the server 210 through a communication link 260. The communication link 260 might include any suitable network connection employed. Presently preferred network configurations include both proprietary or dedicated networks, as well as open networks, such as the Internet. Data may be exchanged between the server 210 and the identification device 255 in any suitable format, such as in accordance with the Internet Protocol (IP), the Transmission Control Protocol (TCP), or other known protocols. Moreover, certain of the data may be transmitted or formatted via markup languages such as the HyperText Markup Language (HTML), or other standard languages.

The identification device 255 communicates with the server 210 for obtaining navigation information. The identification device 255 communicates the current patient location and destination information to the server 210. The destination information may be a desired facility location or a desired resource location in the facility.

In an embodiment, the processor 214 based on the current patient location and the desired destination, the navigation information is calculated. The navigation information might include distance and direction to desired destination from the current patient location. The navigation information may be sent to the identification device 255 through the communication link 260. The identification device 255 communicates the navigation information to the patient 250 aurally or visually.

In an embodiment, once the communication is established with identification device 255 and the server 210, the server 210 may send the map to the identification device 255. The patient identification device 255 may store the map in its memory.

Figure 3:
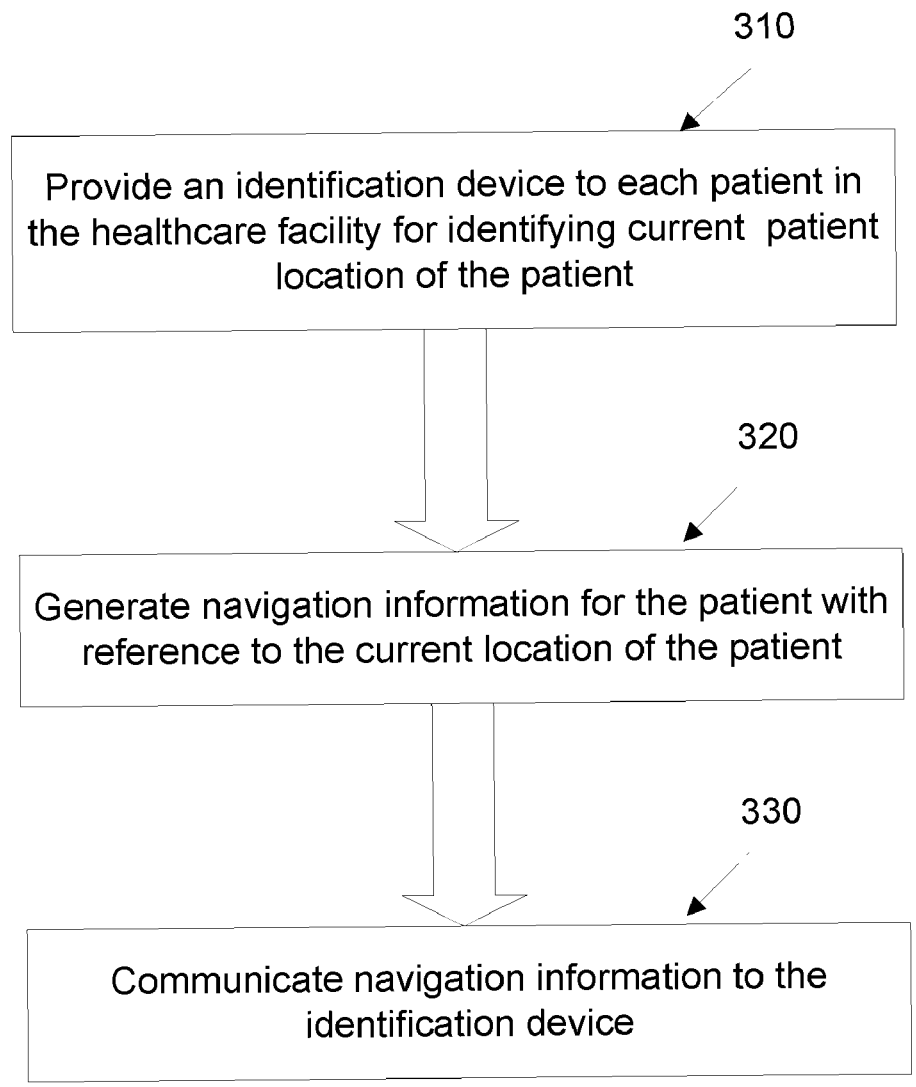
FIG. 3 is a flowchart illustrating a method of facilitating automated navigation in a healthcare environment as described in an embodiment of the invention.

FIG. 3 is a flowchart illustrating an automatic navigation method as described in an embodiment of the invention. At step 310, an identification device is provided to each patient in the healthcare facility. The identification device is a configurable device and could be configured with a unique identification number derived from the patient information. The identification device identifies the current location of the patient. The identification device may communicate the current location of the patient to a healthcare information system (HIS). The identification device could also be protected using a password. In an example, the HIS could include a server associated with a database and a processor. At step 320, navigation information to a destination is generated with reference to the current patient location. The destination indicates the destination to which the patient needs to be navigated. This could be provided by the identification device or by an administrator. The server may access a database having patient information, healthcare resource information, and healthcare facility information. The server may also have an interactive healthcare facility map indicating the location of various resources and healthcare facility. This may be communicated to the identification device by the server, upon establishing communication between the server and the identification device. In an embodiment, the navigation information may be generated by a processor associated with the server, if the identification device is in communication with the server. Alternately, the identification device itself may generate the navigation information. For this the identification device uses the interactive facility map stored in its memory. Using the map and based on the current patient location, which is identified by the identification device, the identification device may generate the navigation information. At step 330, the navigation information is communicated to the patient. If the server is generating the navigation information such as distance and direction to the destination, the same may be communicated to the identification device.

The identification device has various displaying method using which, the navigation information may be displayed to the patient.

Figure 4A:
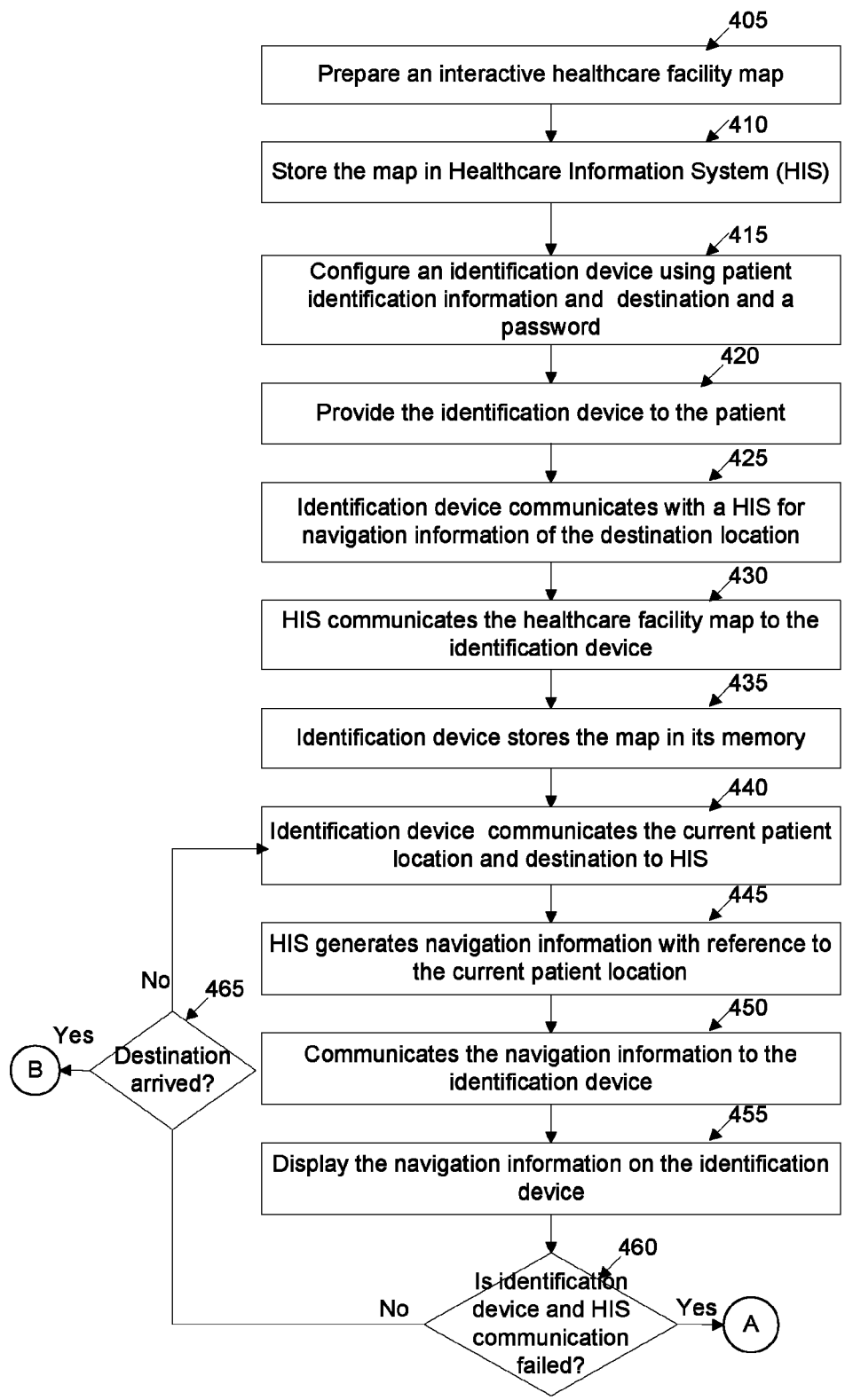
FIGS. 4A and 4B show a detailed flowchart illustrating a method of facilitating automated navigation in a healthcare environment as described in an embodiment of the invention.
Figure 4B:
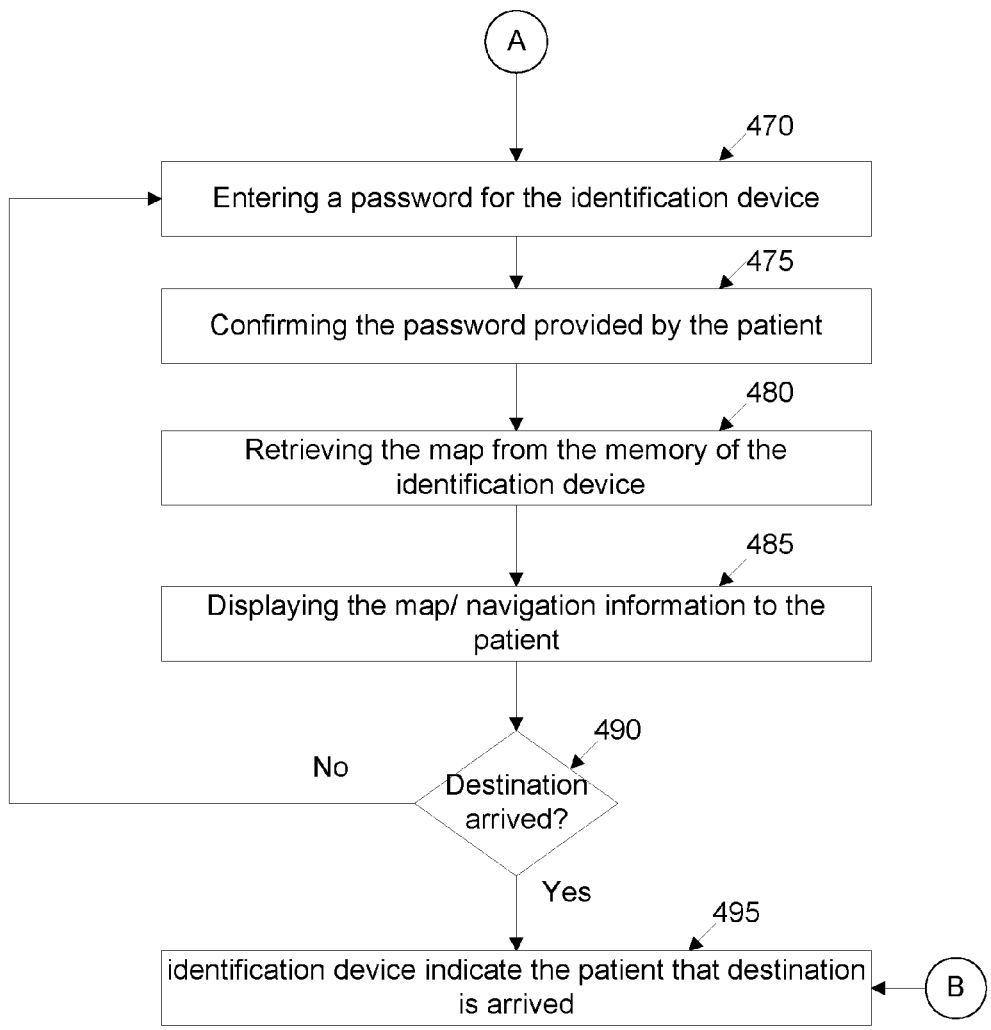

FIG. 4 is a detailed flowchart illustrating a method of facilitating automated navigation in a healthcare environment as described in an embodiment of the invention. At step 405, an interactive healthcare facility map is prepared. This could be done by a healthcare information system or could be done by an administrator. At step 410, the interactive healthcare facility map is stored with the HIS. At step 415, an identification device is configured using patient information and a password. This will ensure that the identification device is configured with a unique identification number corresponding to the patient. In an embodiment, the administrator may also provide a destination to the identification device. At step 420, the configured identification device is provided to the patient. The identification device is configured to track the current position of the patient. At step 425, the identification device communicates the current location of the patient and the destination to the HIS. At step 430, HIS communicates the interactive healthcare facility map to the identification device. The healthcare facility map indicates details of healthcare facility along with the location of various healthcare resources. This may also have directional details. The identification device is configured to store this map in its memory as shown at step 435. At step 440, the identification device communicates the patient's current location and destination to the HIS. The HIS generates navigation information of the destination with reference to the current patient location, as at step 445. The navigation information such as the distance and direction to the destination from the patient's current location is being communicated to the identification device, as step 450. At step 455, the navigation information is displayed in the identification device. This may be displayed in audio or visual format. At step, 460, a check is made to ensure that the HIS and the identification device are still communicating. If they are still communicating, a check is made at step 465, to check whether the patient reached the destination. If not, the steps from 440-460 have been repeated until the patient reaches his destination. If the patient reached his destination, the identification device indicates the same as at step 495. However if the communication between the identification device and the HIS is lost, then the patient will be navigated with the help of the identification device. This illustrated in step 470-495. At step 470, a password is entered to the identification device, to ensure the proper usage of the identification device by the authorized person only. At step 475, the identification device confirms the password provided by the patient. At step 480, the healthcare facility map is being retrieved from the memory of the identification device. The navigation information calculated by the identification device or the map retrieved from the memory might be displayed to the patient as at step 485. A check is made to confirm whether the patient arrived his destination and if not, the process may repeat the steps from 470 to 490. Upon arriving the destination, the identification device indicates that the patient has reached the destination as at step 495.

Figure 5:
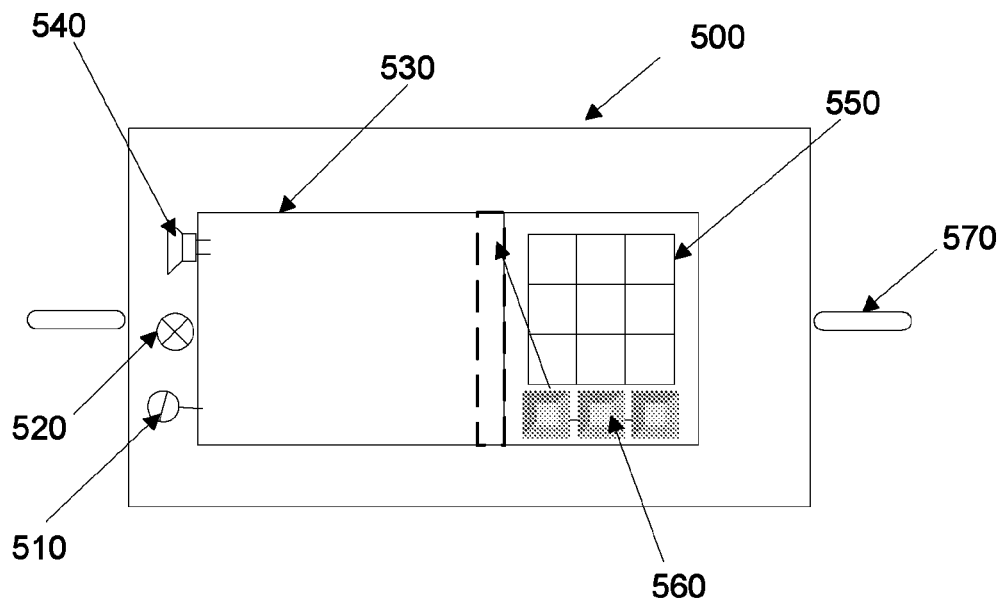
FIG. 5 is diagrammatic illustration of an identification device as described in an embodiment of the invention.

FIG. 5 is diagrammatic illustration of an identification device as described in an embodiment of the invention. The identification device 500 is configured to identify a patient by providing the current location of the patient. The identification device 500 is configured to include a tracking device 510 configured to track the patient. The tracking device 510 may be an RFID, IR, GPS, Barcode associated device that is capable of identifying the location of the patient. A communication interface 520 is provided to communicate the identified patient location to an external device. The communication interface 520 may be a port, which could help the identification device 500 to communicate wirelessly or through a cable with different external devices. The identification device 500 is further provided with a display 530 configured to display navigation information or any other relevant information provided by an external device through the communication interface 520. Also, the navigation information may be communicated in audio format using an audio speaker 540. The identification device 500 may be further provided with keypad 550 using which various queries can be typed by the patient and send it to the external device. Also the identification device 500 includes various configurable buttons 560 such as emergency button configured to send some queries or information to an external device. The identification device may be further provided with a connecter 570 using which the identification device 500 can be connected to the patient.

Further more, the identification device 500 may have a memory and a processor (not shown). The memory may be used to store various information provided by external devices and processor may process the information provided by the external devices. The processor may include multi-processor systems, microprocessor-based or programmable consumer electronics, minicomputers etc.

In an embodiment, the external device is a healthcare information system configured to communicate with the identification device 500 wirelessly. The memory may store a healthcare facility map and the processor may generate navigation information corresponding to a destination using the map.

Figure 6A:
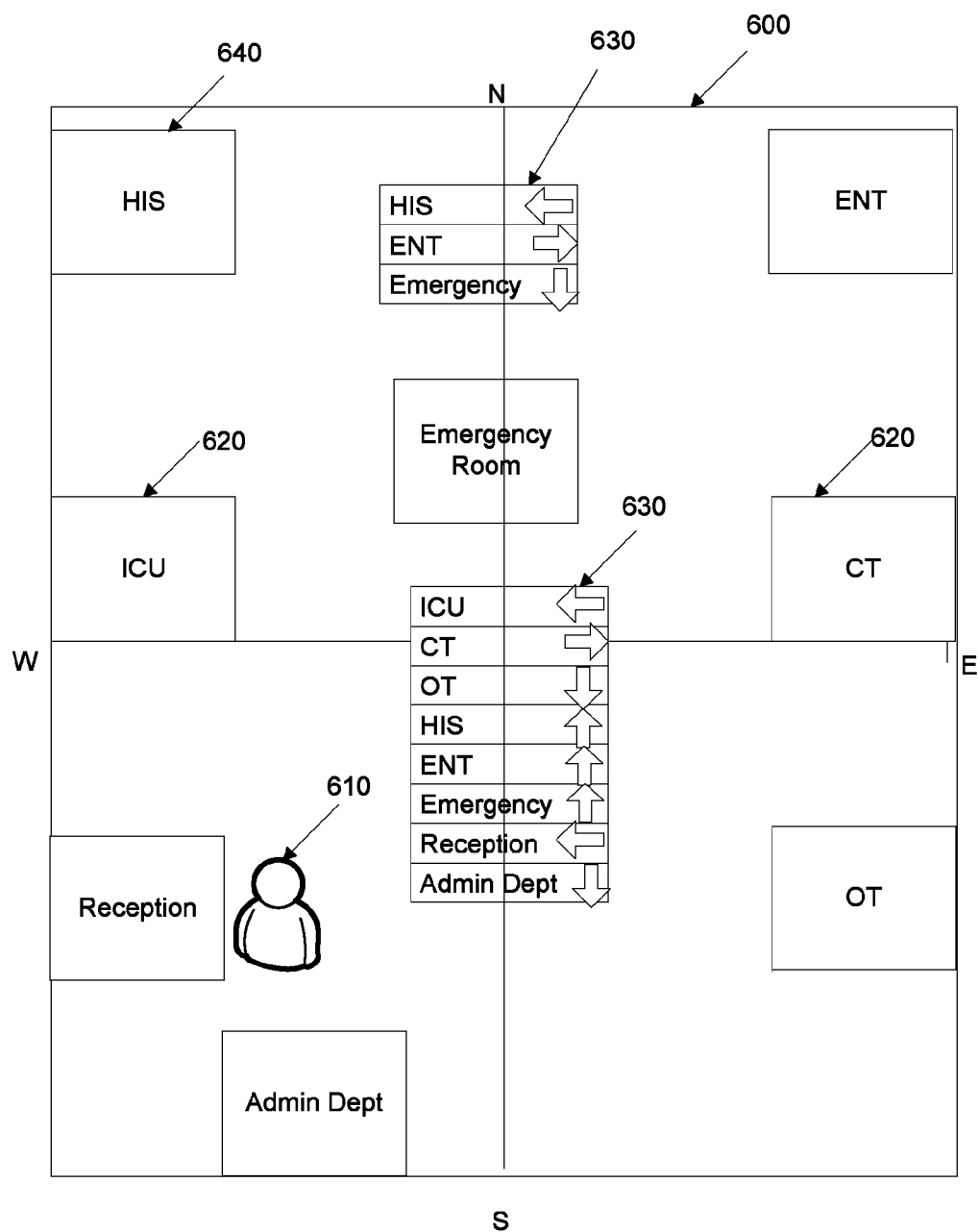
FIGS. 6A and 6B are diagrammatic illustrations of navigating in a conventional healthcare environment and in a healthcare environment as described in an embodiment of the invention.
Figure 6B:
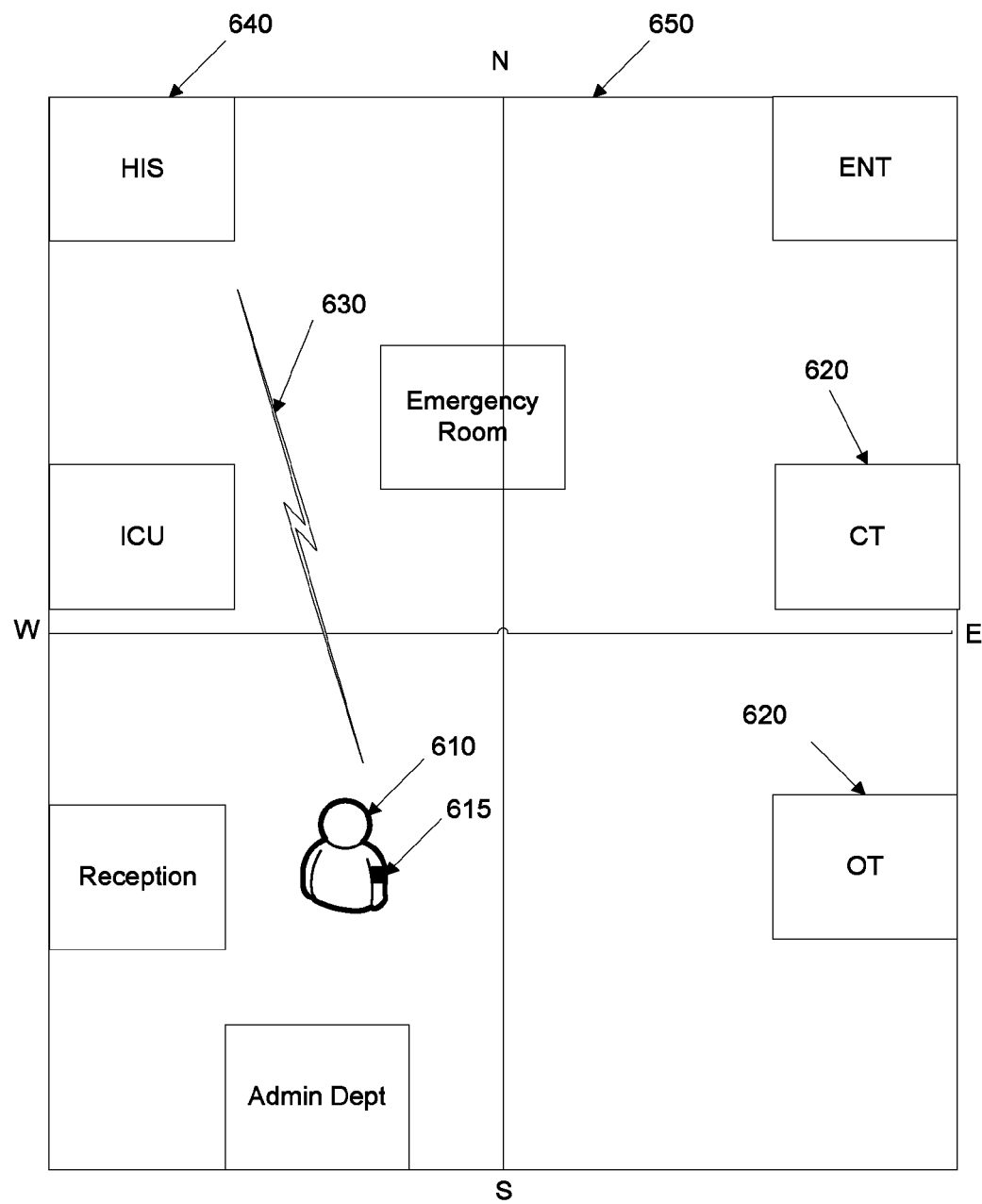

FIGS. 6A and 6B are diagrammatic illustrations of navigating in a conventional healthcare environment and in a healthcare environment as described in an embodiment of the invention. FIG. 6A illustrates a navigation method in a conventional healthcare environment. The healthcare environment 600 is configured to include various resources such as CT (Computed Tomography), HIS etc and various facilities such as reception, Admin department, ENT (Ear, Nose, Throat) department, ICU (Intensive Care Unit), emergency patient care room etc. Various resources and facilities in a healthcare environment need to be limited to these example and they are represented as 620. A patient 610 is configured to navigate to various locations 620 in the healthcare environment 600. The patient 610 takes the help of various sign boards 630 displayed at various parts of the healthcare environment 600 to navigate to a desired destination. The healthcare environment 600 further includes a healthcare information system 640. The healthcare information system 640 is stored with various healthcare resource, healthcare facility and patient information. FIG. 6B illustrates an automated navigation method in a healthcare environment. The healthcare environment 650 includes various resource and facilities represented as 620. A patient 610 is provided with an identification device 615, the identification device 615 is configured to identify the current location of the patient. The healthcare environment 600 further includes a healthcare information system 640. The healthcare information system 640 is stored with various healthcare resource, healthcare facility and patient information. The identification device 615 interacts with the HIS 640 through a communication link 630. The identification device 615 conveys the patient's current location and based on the same, the HIS 640 generates navigation information for a destination and sent it to the identification device 615. Based on the displayed navigation information, the patient 610 navigates to the destination.

Figure 7:
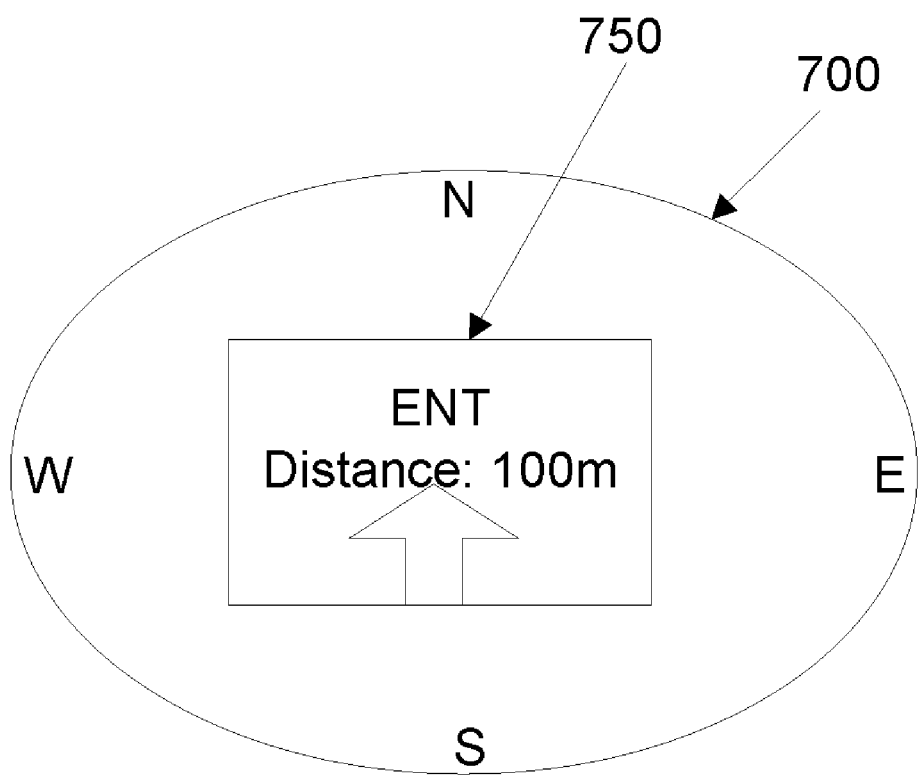
FIG. 7 is a diagrammatic representation of a model of navigation information displayed in an identification device.
Figure 2:
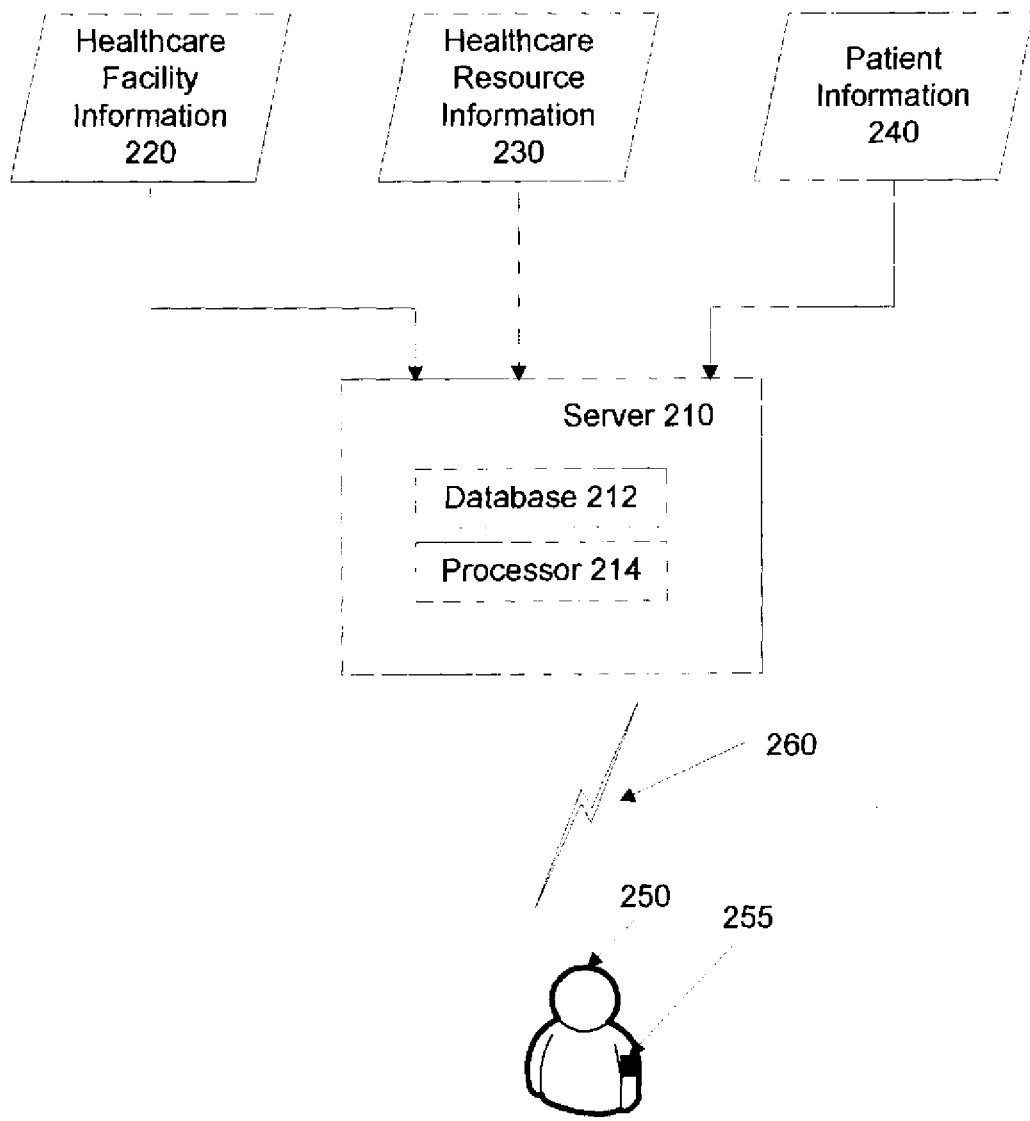

A model of navigation information display in an identification device is shown in FIG. 7. In an identification device 700, navigation information 750 is displayed. The navigation information 750 includes destination location along with the distance and direction from the current location is displayed. However the image display need to be limited to the example or the format shown. It could also display different parameters such as estimated time to reach the destination or any other relevant information about the destination.

The advantages of the invention include providing an automated and cost effective navigation method. The navigation system needs identification device only with the patient and do not need it at the destinations. Since identification devices at destinations are not required at all, destination location data is not required to be saved on identification device. Since the identification device is used only with the patient, its more cost effective. Also the maintainability is easy. This is because, in case of any updates, the administrator may update the HIS automatically or manually and the same may be communicated to the patient automatically. Another advantage is since the map is stored with the identification device, in the event of a communication failure or if the HIS is not responding, the identification device may itself derive the navigation information. Further, it will save time for patient as well as hospital staff, as the patient is directly going to required destination without any help from sign boards or hospital staff.

In yet other embodiments of the present invention, a machine readable medium or media may include, but not limited to, magnetic disks and diskettes, optical disks and diskettes, and/or ROM, flash ROM, and/or battery backed RAM, or any other suitable magnetic, optical, or electronic medium or media). The medium (or media) has recorded thereon instructions configured to instruct a system that includes a server and an identification device. The instructions include instructions for obtaining the current location of a patient in a healthcare facility from an identification device provided to the patient. The media further includes instructions for generating navigation information to a destination, for the patient with reference to the current location of the patient and instructions for communicating the navigation information to the identification device. This will facilitate automatic navigation in a healthcare environment.

However software and/or firmware (hereinafter referred to generically as "software") can be used to instruct the computer to perform the inventive combination of actions described herein. Further, in some embodiments, this may comprise one or more electronic hardware components or special-purpose hardware components that may be configured to perform the same purpose as a software module or to aid in the performance of the software module.

The above-description of the embodiments of the methods and systems has the technical effect of assisting a patient to navigate automatically in a healthcare environment.

Thus various embodiments of the invention describe a method and system for facilitating automated navigation in a healthcare environment.

As used herein, an element or step recited in the singular and proceeded with the word "a" or "an" should be understood as not excluding plural elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property. Moreover, the terms "computer" and "processor" are used interchangeably herein to refer to either specialized hardware to perform digital signal processing, control, data manipulation, and/or calculations, or a general purpose computer that can be programmed to perform the same functions and/or adapted to interface with external digital signals. The phrases "computer or processor" and "processor or computer" are therefore intended to have equal scope with either of the individual terms and are not intended to imply a dichotomy between the two terms.

Exemplary embodiments are described above in detail. The assemblies and methods are not limited to the specific embodiments described herein, but rather, components of each assembly and/or method may be utilized independently and separately from other components described herein. Further the steps involved in the workflow need not follow the sequence in which there are illustrated in figures and all the steps in the work flow need not be performed necessarily to complete the method.

While the invention has been described with reference to preferred embodiments, those skilled in the art will appreciate that certain substitutions, alterations and omissions may be made to the embodiments without departing from the spirit of the invention. Accordingly, the foregoing description is meant to be exemplary only, and should not limit the scope of the invention as set forth in the following claims.

What is claimed is:

1. A system for assisting a patient in navigating within a healthcare environment, the system comprising:
    a healthcare information system configured to have access to at least patient information, healthcare resource information and healthcare facility information; and
    an identification device configured to be provided to a patient in the healthcare facility, and further configured to communicate at least a current location of the patient to the hospital information system, the identification device comprising a memory, and the memory of the identification device configured to store a healthcare facility map,
    wherein the identification device and the healthcare information system are configured to interact with each other to generate and provide at least navigation information to the patient, and
    wherein the identification device is configured to retrieve the healthcare facility map from its memory upon losing communication with the hospital information system.

2. The system in accordance with claim 1, wherein the healthcare information system is configured to generate and communicate the healthcare facility map to the identification device.

3. The system in accordance with claim 1, wherein the identification device is a configurable device configured to initiate the interaction by querying the healthcare information system for navigation information corresponding to a destination.

4. The system in accordance with claim 3, wherein the navigation information includes: distance and direction to the destination from the current location of the patient, the destination being a desired healthcare resource or healthcare facility.

5. The system in accordance with claim 4, wherein the healthcare information system is configured to generate the navigation information with reference to the current location of the patient.

6. The system in accordance with claim 1, wherein the identification device includes a Radio frequency identification tag (RFID) based tracking device, Global positioning system (GPS) based tracking device, Infrared (IR) based tracking device and barcode based tracking device.

7. The system in accordance with claim 1, wherein the identification device further comprises a display configured to convey the navigation information to the patient.

8. The system in accordance with claim 1, wherein the identification device is further configured to communicate an emergency situation of the patient to the hospital information system.

9. The system in accordance with claim 8, wherein the healthcare information system is configured to identify a nearest emergency patient care room to the patient's, current location and communicate the same to the patient.

10. The system in accordance with claim 9, wherein the healthcare information system is further configured to communicate the patient information to the nearest emergency room and establish a communication between the patient and emergency room.

11. The system in accordance with claim 10, wherein the healthcare information system is further configured to convey any relevant information corresponding to the destination to the identification device.

12. The system in accordance with claim 11, wherein the healthcare information system is a server configured to be associated with a database and a processor.

13. An automated navigation method in a healthcare environment wherein an identification device is provided to a patient in a healthcare facility of the healthcare environment, and wherein the identification device is configured to interact with a healthcare information system, store a healthcare facility map in a memory and identify a current location of the patient, the method comprising:
    generating navigation information for the patient with reference to the current location of the patient;
    communicating the navigation information to the identification device; and
    retrieving the healthcare facility map from the memory of the identification device upon losing communication with the hospital information system.

14. The method in accordance with claim 13, wherein the identification device is configured to have a unique identification number specific to the patient.

15. The method in accordance with claim 13, wherein the identification device further comprises a password.

16. The method in accordance with claim 13, wherein the step of generating navigation information comprises:
    accessing a database having patient information, healthcare resource information, healthcare facility information, and the healthcare facility map.

17. The method in accordance with claim 13, wherein the step of generating navigation information further comprises:
    obtaining destination information, indicating the destination to which the patient needs to be navigated.

18. The method in accordance with claim 17, wherein the step of generating navigation information further comprises:
    generating distance and direction for a patient to navigate to the destination.

19. The method in accordance with claim 13, wherein the step of communicating the navigation information to the identification device comprises:
    communicating the navigation information to the identification in text, audio and image format.

20. A non-transitory machine readable, medium or media having recorded thereon instructions configured to instruct an apparatus comprising a server and an identification device for automatically navigating in a healthcare facility, wherein the identification device is provided to a patient in a healthcare facility, and wherein the identification device is configured to interact with the server and store a healthcare facility map in a memory of the identification device, the machine readable medium or media comprising:

a routine for obtaining the current location of a patient in a healthcare facility from the identification device;

a routine for generating navigation information to a destination, for the patient with reference to the current location of the patient;

a routine for communicating the navigation information to the identification device; and a routine for retrieving the healthcare facility map from the memory of the identification device upon losing communication with the server.

* * * * *

UNITED STATES PATENT AND TRADEMARK OFFICE
CERTIFICATE OF CORRECTION

| | | |
|---|---|---|
| PATENT NO. | : 8,334,767 B2 | |
| APPLICATION NO. | : 12/634716 | |
| DATED | : December 18, 2012 | |
| INVENTOR(S) | : Jain et al. | |

It is certified that error appears in the above-identified patent and that said Letters Patent is hereby corrected as shown below:

In the Drawings

Delete drawing sheet 2 of 9, and replace with drawing sheet 2. (attached)

In the Specification

In Column 2, Line 51, delete "is" and insert -- is a --, therefor.

In Column 8, Line 58, delete "is" and insert -- is a --, therefor.

In the Claims

In Column 12, Line 29, in Claim 13, delete "memory" and insert -- memory, --, therefor.

In Column 12, Line 61, in Claim 20, delete "readable," and insert -- readable --, therefor.

Signed and Sealed this
Seventeenth Day of September, 2013

Teresa Stanek Rea
*Deputy Director of the United States Patent and Trademark Office*